United States Patent

Maywald et al.

[11] Patent Number: 5,576,270
[45] Date of Patent: Nov. 19, 1996

[54] ISOXAZOLECARBOXAMIDES, THEIR PREPARATION AND THEIR USE

[75] Inventors: Volker Maywald, Ludwigshafen; Thomas Kuekenhoehner, Boehl-Iggelheim; Peter Muenster, Neulussheim; Wolfgang von Deyn, Neustadt; Helmut Walter, Obrigheim; Matthias Gerber, Limburgerhof; Karl-Otto Westphalen, Speyer; Uwe Kardorff, Mannheim, all of Germany

[73] Assignee: BASF Aktiengesellschaft, Ludwigshafen, Germany

[21] Appl. No.: 313,176

[22] PCT Filed: Apr. 16, 1994

[86] PCT No.: PCT/EP93/00918

§ 371 Date: Sep. 29, 1994

§ 102(e) Date: Sep. 29, 1994

[87] PCT Pub. No.: WO93/22295

PCT Pub. Date: Nov. 11, 1993

[30] Foreign Application Priority Data

Apr. 29, 1992 [DE] Germany ............. 42 14 010.2

[51] Int. Cl.$^6$ ............. A61K 31/42; C07D 261/06
[52] U.S. Cl. ............. 504/271; 514/378; 548/248
[58] Field of Search ............. 548/248; 514/378; 504/271

[56] References Cited

U.S. PATENT DOCUMENTS 5,001,124  3/1991  Patterson et al. ............. 514/236.8
5,201,932  4/1993  Maywald et al. ............. 504/271
5,371,099  12/1994  Bartlett et al. ............. 514/378

OTHER PUBLICATIONS

Shimizu, T.; Hayashi, Y.; and Teramura, K.; Bull. Chem. Soc. Jpn., 58, 2519–2522 Sep. (1985).

Kim, J. N.; and Ryu, E. K.; Heterocycles, vol. 31, No. 9, 1693–1697 (1990). Month not available.

Primary Examiner—Johann Richter
Assistant Examiner—Laura L. Stockton
Attorney, Agent, or Firm—Keil & Weinkauf

[57] ABSTRACT

The invention pertains to isoxazolecarboxamides of the formula I

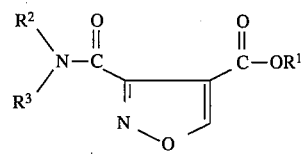

where
$R^1$ is alkyl, cycloalkyl, alkoxyalkyl, alkenyl, alkynyl, phenyl or unsubstituted or substituted benzyl,
$R^2$ is hydrogen or alkyl and
$R^3$ is alkyl, cycloalkyl, alkenyl, alkynyl, phenyl or unsubstituted or substituted benzyl,
and the plant-tolerated salts of those compounds in which $R^2$ is hydrogen, their preparation and their use.

5 Claims, No Drawings

ISOXAZOLECARBOXAMIDES, THEIR PREPARATION AND THEIR USE

This application is a 371 of PCT/EP93/00918 filed Apr. 16, 1994 and published as WO93/22295 Nov. 11, 1993.

The present invention relates to isoxazolecarboxamides of the formula I

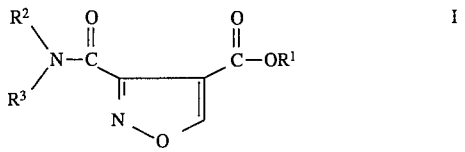

where
$R^1$ is
- (a) $C_1$–$C_6$-alkyl which may carry from one to five halogen atoms and/or up to three hydroxyl and/or $C_1$–$C_4$-alkoxy groups and/or one of the following radicals:
  cyano;
  $C_1$–$C_4$-alkoxy-$C_2$–$C_4$-alkoxy;
  $C_1$–$C_3$-alkylthio;
  $C_1$–$C_3$-alkylamino, di-$C_1$–$C_3$-alkylamino;
  $C_3$–$C_6$-cycloalkylamino or di-$C_3$–$C_6$-cycloalkylamino;
  tri-$C_1$–$C_4$-alkylsilyl;
  carboxyl, $C_1$–$C_3$-alkoxycarbonyl or $C_1$–$C_3$-alkoxycarbonyl-$C_1$–$C_3$-alkoxy, di-($C_1$–$C_3$-alkyl)-aminocarbonyl;
  $C_1$–$C_6$-alkyliminoxy or $C_5$- or $C_6$-cycloalkyliminoxy;
  a 5-membered or 6-membered saturated or unsaturated heterocyclic radical, each having up to 3 hetero atoms selected from the group consisting of oxygen, sulfur and nitrogen, where two oxygen and/or sulfur atoms cannot be directly adjacent and where the heterocycles may furthermore carry one or two of the following substituents: halogen, $C_1$–$C_3$-alkyl or $C_1$–$C_3$-alkoxy;
  $C_3$–$C_6$-cycloalkyl;
  phenyl which may furthermore carry up to three of the following substituents: halogen, nitro, cyano, $C_1$–$C_6$-alkyl, partially or completely halogenated $C_1$–$C_3$-alkyl, $C_1$–$C_3$-alkoxy or partially or completely halogenated $C_1$–$C_3$-alkoxy;
  —$CR^{10}$=N-$R^{11}$, where
    $R^{10}$ is hydrogen or $C_1$–$C_6$-alkyl and
    $R^{11}$ is $C_1$–$C_6$-alkoxy, $C_3$–$C_6$-alkenyloxy or $C_3$–$C_6$-alkynyloxy, each of which may carry up to three halogen atoms and/or a phenyl radical having, if desired, up to three of the following radicals: halogen, nitro, cyano, $C_1$–$C_3$-alkyl or $C_1$–$C_3$-alkoxy;
  $C_1$–$C_6$-alkylamino, di-$C_1$–$C_6$-alkylamino or phenylamino, where the phenyl radical may additionally carry up to three of the following radicals: halogen, nitro, cyano, $C_1$–$C_3$-alkyl or $C_1$–$C_3$-alkoxy;
- (b) $C_3$–$C_8$-cycloalkyl which may carry from one to five of the following radicals: halogen, $C_1$–$C_4$-alkyl, $C_1$–$C_4$-alkoxy, partially or completely halogenated $C_1$–$C_4$-alkyl or partially or completely halogenated $C_1$–$C_4$-alkoxy;
- (c) branched or straight-chain $C_3$–$C_6$-alkenyl which is unsubstituted or substituted by $C_3$–$C_6$-alkynyl, halogen, $C_1$–$C_4$-alkoxy or phenyl,
- (d) $C_5$- or $C_6$-cycloalkenyl,
- (e) branched or straight-chain $C_3$–$C_6$-alkynyl which is unsubstituted or substituted by halogen, $C_1$–$C_4$-alkoxy or phenyl, where the phenyl radical in turn may carry from one to three of the following groups: halogen, nitro, cyano, $C_1$–$C_4$-alkyl, partially or completely halogenated $C_1$–$C_4$-alkyl, $C_1$–$C_4$-alkoxy or partially or completely halogenated $C_1$–$C_4$-alkoxy;
- (f) phenyl which may carry from one to three of the following groups: halogen, nitro, cyano, $C_1$–$C_4$-alkyl, partially or completely halogenated $C_1$–$C_4$-alkyl, $C_1$–$C_4$-alkoxy or partially or completely halogenated $C_1$–$C_4$-alkoxy;
- (g) N-phthalimido, tetrahydrophthalimido, N-succinimido or maleimido;
- (h) —N=$CR^8R^9$, where $R^8$ and $R^9$ are each hydrogen, $C_1$–$C_4$-alkyl, $C_3$–$C_6$-cycloalkyl, $C_1$–$C_4$-alkoxy or phenyl which may additionally carry up to three of the following substituents: halogen, nitro, cyano, $C_1$–$C_3$-alkyl, partially or completely halogenated $C_1$–$C_3$-alkyl, $C_1$–$C_3$-alkoxy or partially or completely halogenated $C_1$–$C_3$-alkoxy; or $R^8$ and $R^9$ together are a methylene chain having 4 to 7 methylene groups;

$R^2$ is hydrogen or $C_1$–$C_6$-alkyl;

$R^3$ is
- (a) $C_1$–$C_6$-alkyl which may carry from one to three of the following radicals: halogen, cyano, $C_1$–$C_4$-alkoxy, $C_3$–$C_8$-cycloalkyl or phenyl, where the phenyl ring in turn may carry from one to three of the following radicals: halogen, $C_1$–$C_4$-alkyl, partially or completely halogenated $C_1$–$C_4$-alkyl, $C_1$–$C_4$-alkoxy or partially or completely halogenated $C_1$–$C_4$-alkoxy;
  $C_3$–$C_8$-cycloalkyl which may carry from one to three of the following radicals: halogen, $C_1$–$C_6$-alkyl, partially or completely halogenated $C_1$–$C_6$-alkyl, $C_1$–$C_4$-alkoxy or partially or completely halogenated $C_1$–$C_4$-alkoxy;
- (c) branched or straight-chain $C_3$–$C_8$-alkenyl or branched or straight-chain $C_3$–$C_8$-alkynyl, each of which may be monosubstituted to trisubstituted by halogen and/or monosubstituted by phenyl, where the phenyl radical in turn may carry from one to three of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, cyano or nitro;
- (d) phenyl which may carry from one to four of the following groups: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, halogen, nitro, cyano, formyl, $C_1$–$C_4$-alkanoyl, $C_1$–$C_4$-haloalkanoyl or $C_1$–$C_4$-alkoxycarbonyl;

and the plant-tolerated salts of those compounds in which $R^2$ is hydrogen.

The present invention furthermore relates to herbicides which contain these compounds, processes for the preparation of these compounds and a general process for the preparation of isoxazolecarboxylic acid derivatives of the formula I'

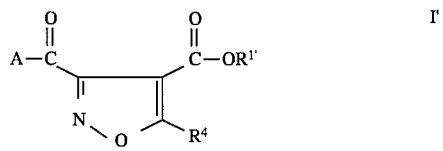

where
$R^{1'}$ is unsubstituted or substituted alkyl, cycloalkyl, phenyl, alkenyl or alkynyl;

A is $NR^{2'}R^{3'}$ or $OR^5$;

$R^{2'}$ is hydrogen or alkyl;

$R^{3'}$ is unsubstituted or substituted alkyl, cycloalkyl, phenyl, alkenyl, alkynyl or aryl;

or $R^{2'}$ and $R^{3'}$ together form $-CH_2CH_2CH_2CH_2-$ or $-CH_2CH_2CH_2CH_2CH_2-$, in which chains a $CH_2$ group may be replaced by oxygen, sulfur or $NCH_3$;

$R^5$ is unsubstituted or substituted alkyl, cycloalkyl, phenyl, alkenyl or alkynyl;

$R^4$ is hydrogen or alkyl, wherein an enamine of the formula II

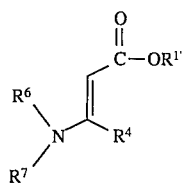

where $R^6$ and $R^7$ are each hydrogen or $C_1$–$C_4$-alkyl or together form $-CH_2CH_2CH_2CH_2-$ or $-CH_2CH_2CH_2CH_2CH_2-$, in which chains a $CH_2$ group may be replaced with oxygen, sulfur or $NCH_3$, is reacted with a hydroxamoyl chloride of the formula III

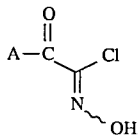

EP-A 418,667 discloses isoxazolecarboxamides as herbicidal active ingredients whose general formula covers the compounds I. However, examples of the specific structure I are not given in this publication.

It is an object of the present invention to provide novel herbicidal active ingredients having improved properties.

We have found that this object is achieved by the compounds I defined at the outset, herbicides which contain these compounds I and processes for their preparation and use.

An improved process for the preparation of the compounds of the general formula I' has also been found.

Compared with prior art compounds, the novel compounds have no substituent in the 5-position of the isoxazole ring. In particular, the combination of hydrogen in the 5-position with an ester group in the 4-position is essential for the advantageous herbicidal action, the type of ester playing no particular role, ie. $R^1$ being very widely variable.

U.S. Pat. No. 3,699,117 disclosed that 5-bisalkoxymethylisoxazole-3,4-dicarboxylates are obtainable by reacting α-chloroximinoacetates with enamines of γ,γ-dialkoxyacetoacetates.

In the formula II, $R^6$ and $R^7$ are each hydrogen or $C_1$–$C_4$-alkyl, such as methyl, ethyl, propyl, 1-methylethyl, butyl, 1-methylpropyl, 2-methylpropyl or 1,1-dimethylethyl, preferably 1-methylethyl, 1-methylpropyl or 1,1-dimethylethyl, or $R^6$ and $R^7$ together are $-CH_2CH_2CH_2CH_2-$ or $-CH_2CH_2CH_2CH_2CH_2-$, in which chains a $CH_2$ group may be replaced with oxygen, sulfur or $NCH_3$, for example $-CH_2OCH_2CH_2-$, $-CH_2SCH_2CH_2-$, $-CH_2N(CH_3)CH_2CH_2-$, $-CH_2CH_2OCH_2CH_2-$, $-CH_2CH_2SCH_2CH_2-$, $-CH_2CH_2N(CH_3)CH_2CH_2-$, $-CH_2OCH_2CH_2CH_2-$, $-CH_2SCH_2CH_2CH_2-$ and $-CH_2N(CH_3)CH_2CH_2CH_2-$, preferably $-CH_2CH_2CH_2CH_2-$, $-CH_2CH_2CH_2CH_2CH_2-$, $-CH_2CH_2OCH_2CH_2-$ or $-CH_2CH_2SCH_2CH_2-$.

This reaction is usually carried out at from 10° to 120° C., preferably from 25° to 70° C.

Suitable solvents are aliphatic hydrocarbons, such as pentane, hexane, cyclohexane and petroleum ether, aromatic hydrocarbons, such as toluene, o-, m- and pxylene, halohydrocarbons, such as methylene chloride, chloroform and chlorobenzene, ethers, such as diethyl ether, diisopropyl ether, tert-butyl methyl ether, dioxane, anisole and tetrahydrofuran, and dimethyl sulfoxide and dimethylformamide, particularly preferably ethers as stated above. Mixtures of the stated solvents may also be used.

The reaction can be carried out in the presence or absence of an HCl-binding base, for example of a tertiary amine. In a preferred embodiment of the process, the addition of a base is dispensed with.

The starting materials are reacted with one another in general in equimolar amounts. However, using an excess of one of the components may be advantageous for the yield.

The enamines II required for the novel process are either commercially available or can be prepared by generally known processes, for example as described in Chem. Ber. 99 (1966), pp. 2526–2545 (C.A. 65: 15316 d).

The hydroxamoyl chlorides III are known from the literature (cf. for example DE-A1-28 17 838; J. Org. Chem., vol. 48, No. 3, 1983; U.S. Pat. No. 3,557,190) or can be prepared starting from acetoacetamides, for example by the process described in DE-A 19 63 061. By this general process, it is also possible in principle to prepare hydroxamoyl chlorides which have not been described to date in the literature.

The process described above is suitable in particular for the preparation of compounds of the general formula I', where $R^{1'}$ is unsubstituted or substituted alkyl, preferably straight-chain or branched low molecular weight alkyl, such as $C_1$–$C_6$-alkyl, eg. methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular methyl or ethyl;

unsubstituted or substituted cycloalkyl, preferably $C_3$–$C_8$-cycloalkyl, such as cyclopropyl, cyclobutyl, cyclopentyl, cyclohexyl, cycloheptyl or cyclooctyl, in particular cyclopropyl, cyclopentyl or cyclohexyl;

unsubstituted or substituted alkenyl, preferably straight-chain or branched $C_3$–$C_6$-alkenyl, such as 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl;

unsubstituted or substituted alkynyl, preferably straight-chain or branched $C_3$–$C_6$-alkynyl, such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl.

In the abovementioned radicals, some or all of the hydrogen atoms may be replaced with halogen atoms, such as fluorine, chlorine, bromine or iodine, preferably with fluorine and/or chlorine. In addition, these radicals may carry from one to three additional substituents which are stable under the reaction conditions, for example:

unsubstituted or substituted phenyl;

$C_1$–$C_4$ haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy, preferably methoxy or ethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio.

In addition to the abovementioned groups, the cycloalkyl radicals may furthermore carry from one the three of the following radicals:

$C_1$–$C_4$-alkyl, such as methyl, ethyl, propyl, 1-methylethyl, butyl, 1-methylpropyl, 2-methylpropyl or 1,1-dimethylethyl.

The phenyl radical in turn may carry, in addition to the abovementioned halogen atoms, from one to three of the following radicals:

the abovementioned $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio groups and/or $C_1$–$C_4$-alkyl, such as methyl, ethyl, propyl, 1-methylethyl, butyl, 1-methylpropyl, 2-methylpropyl or 1,1-dimethylethyl.

A is $NR^{2'}R^{3'}$ or $OR^5$.

Here, $R^{2'}$ is hydrogen or alkyl as stated above in general and in particular.

$R^{3'}$ is unsubstituted or substituted alkyl, cycloalkyl, alkenyl or alkynyl as stated above in general and in particular, or is unsubstituted or substituted aryl, such as phenyl, 1-naphthyl or 2-naphthyl, in which aromatic radicals some or all of the hydrogen atoms may be replaced with halogen atoms as stated above in general and in particular, and which aromatic groups may furthermore carry from one to three of the following radicals:

$C_1$–$C_4$-alkyl, such as methyl, ethyl, propyl, 1-methylethyl, butyl, 1-methylpropyl, 2-methylpropyl or 1,1-dimethylethyl;

$C_1$–$C_4$-haloalkyl, in particular $C_1$- or $C_2$-haloalkyl, such as chloromethyl, dichloromethyl, trichloromethyl, fluoromethyl, difluoromethyl, trifluoromethyl, chlorofluoromethyl, dichlorofluromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl;

$C_1$–$C_4$-alkoxy, such as methoxy, ethoxy, propoxy, 1-methylethoxy, butoxy, 1-methylpropoxy, 2-methylpropoxy or 1,1-dimethylethoxy;

$C_1$–$C_4$-haloalkoxy, in particular $C_1$- or $C_2$-haloalkoxy, such as chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or pentafluoroethoxy;

$C_1$–$C_4$-alkylthio, such as methylthio, ethylthio, propylthio, 1-methylethylthio, butylthio, 1-methylpropylthio, 2-methylpropylthio or 1,1-dimethylethylthio;

$C_1$–$C_4$-haloalkylthio, in particular $C_1$- or $C_2$-haloalkylthio, such as chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or pentafluoroethylthio.

In addition, $R^{2'}$ and $R^{3'}$ together may be —$CH_2CH_2CH_2CH_2$— or —$CH_2CH_2CH_2CH_2CH_2$—, in which chains a $CH_2$ group may be replaced with oxygen, sulfur or $NCH_3$, for example: —$CH_2OCH_2CH_2$—, —$CH_2SCH_2CH_2$—, —$CH_2N(CH_3)CH_2CH_2$—, —$CH_2CH_2OCH_2CH_2$—, —$CH_2CH_2SCH_2CH_2$—, —$CH_2CH_2NHCH_2CH_2$—, —$CH_2CH_2N(CH_3)CH_2CH_2$—, —$CH_2OCH_2CH_2CH_2$—, —$CH_2SCH_2CH_2CH_2$— and —$CH_2N(CH_3)CH_2CH_2CH_2$—.

$R^5$ is unsubstituted or substituted alkyl, cycloalkyl, phenyl, alkenyl or alkynyl as stated above in general and in particular for $R^{1'}$.

$R^4$ is hydrogen or low molecular weight straight-chain alkyl, in particular $C_1-C_6$-alkyl, such as methyl, ethyl, propyl, butyl, pentyl or hexyl, preferably hydrogen.

In addition to the process described above, conventional processes known from the literature are also suitable for the preparation of the compounds I. The compounds I are particularly preferably obtained starting from alkyl 3-aminocarbonylisoxazole-4-carboxylates, for example $C_1-C_6$-alkyl esters, such as methyl or ethyl esters, by transesterification according to the following equation, by first cleaving the alkyl ester in a conventional manner (cf. J. March, Advanced Organic Chemistry, 2nd Edition, McGraw-Hill International Book Company, 1977, page 349 et seq.) in the presence of a base and then esterifying the resulting acid IV with an alcohol V:

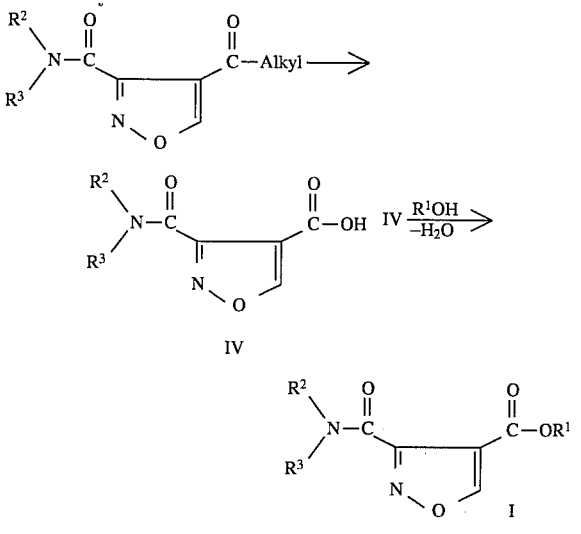

This cleavage of the alkyl ester to give IV is usually carried out at from −10° to 50° C., preferably from 0° to 30° C., in water or an organic solvent.

Suitable solvents are aliphatic hydrocarbons, such as pentane, hexane, cyclohexane and petroleum ether, aromatic hydrocarbons, such as toluene, o-, m- and p-xylene, ethers, such as diethyl ether, diisopropyl ether, tert-butyl methyl ether, dioxane, anisole and tetrahydrofuran, alcohols, such as methanol, ethanol, n-propanol, isopropanol, n-butanol and tert-butanol, and dimethyl sulfoxide, dimethylformamide and water, particularly preferably alcohols as stated above or water.

Mixtures of the stated solvents may also be used.

Suitable bases are generally inorganic compounds, such as alkali metal or alkaline earth metal hydroxides, such as lithium hydroxide, sodium hydroxide, potassium hydroxide or calcium hydroxide, alkali metal or alkaline earth metal oxides, such as lithium oxide, sodium oxide, calcium oxide and magnesium oxide, alkali metal or alkaline earth metal carbonates, such as lithium carbonate, sodium carbonate and calcium carbonate, and alkali metal bicarbonates, such as sodium bicarbonate.

Alkali metal and alkaline earth metal hydroxides, such as sodium hydroxide and potassium hydroxide, are particularly preferred.

The bases are used in general in equimolar amounts or in excess.

If the base is not sufficiently soluble in the solvent used (two-phase reaction procedure), the addition of a phase transfer catalyst, for example a crown ether, to the reaction mixture may also be advantageous with regard to the reaction rate and the yield.

The esterification of the free acid IV with an alcohol V to give the compound I can be carried out by the conventional esterification methods (cf. J. March, Advanced Organic Chemistry, 2nd Edition, McGraw-Hill International Book Company, 1977, page 361 et seq., 363 et seq. and the literature cited there).

Usually, the acid IV is first converted into an activated form, which is then reacted with the alcohol V at from 0° to 100° C., preferably from 25° to 70° C.

Advantageously used solvents are aromatic hydrocarbons, such as toluene, o- m- and p-xylene, halohydrocarbons, such as methylene chloride, chloroform and chlorobenzene, ethers, such as diethyl ether, diisopropyl ether, tert-butyl methyl ether, dioxane, anisole and tetrahydrofuran, ketones, such as acetone, methylethyl ketone, diethyl ketone and tert-butyl methyl ketone, esters of organic acids, such as ethyl acetate, and dimethyl sulfoxide and dimethylformamide. Mixtures of the stated solvents may also be used.

For example, halogen compounds, such as in particular thionyl chloride, oxalyl chloride and phosgene, or dehydrating agents, such as dicyclohexylcarbodiimide, carbonyldiimidazole or acid anhydrides, such as acetic anhydride, propanephosphonic anhydride and 1-methyl-2-halopyridinium iodide (Chem. Lett. (1975), 1045; ibid. (1976), 13; ibid. (1976), 49) are suitable for activating the carboxylic acid IV.

In view of the intended use of the compounds I as herbicides, particularly preferred substances are those in which $R^1$ is (a) $C_1-C_6$-alkyl, preferably $C_1-C_4$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably $C_1-C_4$-alkyl, in particular methyl or ethyl or tert-butyl, which may carry from one to five halogen atoms, such as fluorine, chlorine, bromine or iodine, in particular fluorine or chlorine, and/or up to three hydroxyl and/or $C_1-C_4$-alkoxy groups, such as methoxy, ethoxy, n-propoxy, isopropoxy, n-butoxy and tert-butoxy, and/or one of the following radicals:

cyano, $C_1-C_4$-alkoxy-$C_2-C_4$-alkoxy, in particular methoxyethoxy, ethoxyethoxy or propoxyethoxy, $C_1-C_3$-alkylthio, in particular methylthio or ethylthio, $C_1-C_3$-alkylamino, such as methylamino, ethylamino or isopropylamino, di-$C_1-C_3$-alkylamino, such as dimethylamino, diethylamino, dipropylamino, di-(1-methylethyl)-amino or methylethylamino, $C_3-C_6$-cycloalkylamino or di-$C_3-C_6$-cycloalkylamino, such as cyclopropylamino or dicyclopropylamino, tri-($C_1-C_4$-alkyl)silyl, such as trimethylsilyl or triethylsilyl, carboxyl, $C_1-C_3$-alkoxycarbonyl, such as methoxycarbonyl or isopropoxycarbonyl, $C_1$–$C_3$-alkoxycarbonyl-$C_1$–$C_3$-alkoxy, such as methoxycarbonylmethoxy, di-($C_1$–$C_3$-alkyl)-aminocarbonyl, such as diisopropylaminocarbonyl, $C_1$–$C_6$-alkyliminoxy, such as 2-propyliminoxy, or $C_5$- or $C_6$-cycloalkyliminoxy, such as cyclopentyliminoxy or cyclohexyliminoxy, a 5-membered or 6-membered saturated or unsaturated heterocyclic radical, each having from 1 to 3 hetero atoms selected from the group consisting of oxygen, sulfur and nitrogen, where two oxygen or sulfur atoms or one oxygen and one sulfur atom cannot be directly adjacent, in particular tetrahydrofuran-2-yl, tetrahydrofuran-3-yl, tetrahydrothien-2-yl, tetrahydrothien-3-yl, tetrahydropyran-2-yl, tetrahydropyran-3-yl, tetrahydropyran-4-yl, pyrrolidin-2-yl, pyrrolidin-3-yl, furan-2-yl, furan-3-yl, thien-2-yl, thien-3-yl, pyrrol-2-yl, pyrrol-3-yl, isoxazol-3-yl, isoxazol-4-yl, isoxazol-5-yl, isothiazol-3-yl, isothiazol-4-yl, isothiazol-5-yl, oxazol-2-yl, oxazol-4-yl, oxazol-5-yl, thiazol-2-yl, thiazol-4-yl, thiazol-5-yl, imidazol-2-yl, imidazol-4-yl, imidazol-5-yl, pyrazol-1-yl, pyrazol-3-yl, pyrazol-4-yl, pyrazol-5-yl, 1,2,3-triazol-1-yl, 1,2,3-triazol-4-yl, 1,2,3-triazol-5-yl, 1,2,4-triazol-1-yl, 1,2,4-triazol-3-yl, 1,2,4-triazol-5-yl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazol-3-yl, 1,2,5-thiadiazol-4-yl, 1,3,4-thiadiazol-2-yl, 1,3,4-thiadiazol-5-yl, 1,2,3-oxadiazol-3-yl, 1,2,3-oxadiazol-5-yl, 1,2,4-oxadiazol-3-yl, 1,2,4-oxadiazol-5-yl, 1,2,5-oxadiazol-3-yl, 1,2,5-oxadiazol-4-yl, 1,3,4-oxadiazol-2-yl, 1,3,4-oxadiazol-5-yl, pyrid-2-yl, pyrid-3-yl, pyrid-4-yl, pyrimid-2-yl, pyrimid-4-yl or pyrimid-5-yl, where the heterocycles may furthermore carry one or two of the following substituents: halogen, such as fluorine, chlorine, bromine or iodine, in particular chlorine or bromine and/or $C_1$–$C_3$-alkyl, such as methyl, ethyl, n-propyl or isopropyl, or $C_1$–$C_3$-alkoxy, such as methoxy, ethoxy, n-propoxy or isopropoxy, phenyl which may furthermore carry from one to three of the following substituents: halogen, such as fluorine, chlorine, nitro, bromine or iodine, in particular fluorine or chlorine, nitro, cyano, $C_1$–$C_3$-alkyl, such as methyl or isopropyl, partially or completely halogenated $C_1$–$C_3$-alkyl, such as trifluoromethyl, 1,1,2,2-tetrafluoroethyl or trichloromethyl, $C_1$–$C_3$-alkoxy, such as methoxy or isopropoxy, and/or partially or completely halogenated $C_1$–$C_3$-alkoxy, in particular trifluoromethoxy;

—$CR^{10}$=N—$R^{11}$, where $R^{10}$ is hydrogen or branched or straight-chain $C_1$–$C_6$-alkyl, in particular $C_1$–$C_4$-alkyl, such as methyl, ethyl, n-propyl, isopropyl, n-butyl or tert-butyl;

$R^{11}$ is $C_1$–$C_6$-alkoxy, $C_3$–$C_6$-alkenyloxy or $C_3$–$C_6$-alkynyloxy, in particular $C_1$–$C_4$-alkoxy, such as methoxy, ethoxy, n-propoxy, isopropxy, n-butoxy or tert-butoxy, or prop-2-enyloxy, but-2-enyloxy, prop-2-ynyloxy or but-2-ynyloxy, where these substituents may furthermore carry from one to three halogen atoms, such as fluorine, chlorine, bromine or iodine, in particular fluorine or chlorine, and/or phenyl which is unsubstituted or monosubstituted to trisubstituted by halogen as stated above, nitro, cyano, $C_1$–$C_3$-alkyl, such as methyl, ethyl, n-propyl or isopropyl, and/or $C_1$–$C_3$-alkoxy, such as methoxy, ethoxy, n-propoxy or isopropoxy; phenoxy which may furthermore carry from one to three of the following substituents: nitro, cyano, halogen as stated above, $C_1$–$C_3$-alkyl as stated above and/or $C_1$–$C_3$-alkoxy as stated above; branched or straight-chain $C_1$–$C_6$-alkylamino, di-$C_1$–$C_6$-alkylamino or phenylamino, where the aromatic radical may additionally be mono-substituted to trisubstituted by nitro, cyano, halogen as stated above, $C_1$–$C_3$-alkyl as stated above and/or $C_1$–$C_3$-alkoxy as stated above;

(b) $C_3$–$C_8$-cycloalkyl, preferably $C_3$–$C_6$-cycloalkyl, such as cyclopropyl, cyclopentyl or cyclohexyl;

(c) $C_3$–$C_6$-alkenyl, preferably $C_3$- or $C_4$-alkenyl, such as 2-propenyl or 2-butenyl;

(d) $C_5$- or $C_6$-cycloalkenyl, such as 2-cyclopentenyl or 2-cyclohexenyl;

(e) $C_3$–$C_6$-alkynyl, preferably $C_3$- or $C_4$-alkynyl, such as 2-propynyl, 2-butynyl or 3-butynyl, where the alkynyl group may carry one of the following radicals: halogen, such as fluorine, chlorine, bromine or iodine, $C_1$–$C_4$-alkoxy, such as methoxy or tert-butoxy, or phenyl which in turn may carry from one to three of the following groups: halogen, such as fluorine, chlorine or bromine, nitro, cyano, $C_1$–$C_4$-alkyl, such as methyl, ethyl or tert-butyl, $C_1$–$C_4$-haloalkyl, such as fluoromethyl, trifluoromethyl, chlorodifluoromethyl, pentafluoromethyl or 2-chloro-1,1,2-trifluoromethyl, or $C_1$–$C_4$-alkoxy, such as methoxy, isopropoxy or tert-butoxy;

(f) phenyl which may carry from one to three of the following groups:

halogen, such as fluorine, chlorine, bromine or iodine, in particular fluorine or chlorine, nitro, cyano, $C_1$–$C_4$-alkyl, such as methyl, ethyl or tert-butyl, partially or completely halogenated $C_1$–$C_4$-alkyl, such as trifluoromethyl, 1,1,2,2-tetrafluoroethyl or trichloromethyl, $C_1$–$C_4$-alkoxy, such as methoxy, ethoxy or isopropoxy, or partially or completely halogenated $C_1$–$C_4$-alkoxy, such as trifluoromethoxy, chlorodifluoromethoxy, 1-fluoroethoxy, pentafluoroethoxy or 2-chloro-1,1,2-trifluoroethoxy;

(g) N-phthalimido, tetrahydrophthalimido, N-succinimido or maleimido;

(h) —N=$CR^8R^9$, where $R^8$ and $R^9$ are each hydrogen, $C_1$–$C_4$-alkyl, such as methyl, ethyl, propyl, n-butyl or tert-butyl, $C_3$–$C_6$-cycloalkyl, such as cyclopropyl, cyclopentyl or cyclohexyl, $C_1$–$C_4$-alkoxy as stated above, in particular methoxy, phenyl which may additionally be monosubstituted to trisubstituted by nitro, cyano, halogen as stated above, in particular fluorine or chlorine, $C_1$–$C_3$-alkyl as stated above, in particular methyl, partially or completely halogenated $C_1$–$C_3$-alkyl as stated above, in particular trifluoromethyl, $C_1$–$C_3$-alkoxy as stated above, in particular methoxy, and/or partially or completely halogenated $C_1$–$C_3$-alkoxy as stated above, in particular trifluoromethoxy;

$R^8$ and $R^9$ together are a methylene chain having 4–7, preferably 4 or 5, methylene groups;

$R^2$ is hydrogen or $C_1$–$C_6$-alkyl as stated above, in particular hydrogen;

$R^3$ is (a) branched or straight-chain $C_1$–$C_6$-alkyl, preferably $C_1$–$C_4$-alkyl, such as methyl, ethyl, isopropyl or tert-butyl, which may carry from one to three of the following radicals: halogen, such as fluorine, chlorine or bromine, cyano, $C_1$–$C_4$-alkoxy, such as methoxy or tert-butoxy, $C_3$–$C_8$-cycloalkyl, such as cyclopropyl, cyclopentyl or cyclohexyl, or phenyl which in turn may carry up to three of the following groups: halogen, such as fluorine, chlorine or bromine, $C_1$–$C_4$-alkyl, such as methyl or tert-butyl, $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, partially or completely halogenated $C_1$–$C_4$-alkoxy, such as fluoromethoxy, trichloromethoxy, 2-chloro-1,1,2-trifluoroethoxy or pentafluoroethoxy;

(b) $C_3$–$C_8$-cycloalkyl, preferably $C_3$–$C_6$-cycloalkyl, in particular cyclopropyl, cyclopentyl or cyclohexyl, each of which may carry from one to three of the following radicals: halogen, such as fluorine, chlorine or bromine, $C_1$–$C_6$-alkyl, preferably $C_1$–$C_4$-alkyl, such as methyl or tert-butyl, partially or completely halogenated $C_1$–$C_6$-alkyl, preferably $C_1$–$C_4$-haloalkyl, such as fluoromethyl, trichloromethyl, 2-chloro-1,1,2-trifluoroethyl or pentafluoroethyl, $C_1$–$C_4$-alkoxy, such as methoxy or tert-butoxy, or partially or completely halogenated $C_1$–$C_4$-alkoxy, such as fluoromethoxy, trichloromethoxy, 2-chloro-1,1,2-trifluoroethoxy or pentafluoroethoxy;

(c) branched or straight-chain $C_3$–$C_6$-alkenyl or branched or straight-chain $C_3$–$C_6$-alkynyl, preferably $C_3$- or $C_4$-alkenyl or $C_3$- or $C_4$-alkynyl, such as 2-propenyl, 2-butenyl, 2-propynyl, 1,1-dimethyl-2-propynyl or 3-butynyl, each of which may be monosubstituted to trisubstituted by halogen, such as fluorine, chlorine or bromine, and/or monosubstituted by phenyl, where the phenyl radical in turn may carry from one to three of the following substituents: halogen, in particular fluorine or chlorine, cyano, nitro, $C_1$–$C_4$-alkyl, such as methyl or tert-butyl, partially or completely halogenated $C_1$–$C_4$-alkyl, such as fluoromethyl, trifluoromethyl, trichloromethyl, 2-chloro-1,1,2-trifluoroethyl or pentafluoroethyl, $C_1$–$C_4$-alkoxy, such as methoxy or tert-butoxy, $C_1$–$C_4$-haloalkoxy, such as fluoromethoxy, trifluoromethoxy, trichloromethoxy, 2-chloro-1,1,2-trifluoroethoxy or pentafluoroethoxy, $C_1$–$C_4$-alkylthio, such as methylthio or tert-butylthio, partially or completely halogenated $C_1$–$C_4$-alkylthio, such as fluoromethylthio, trifluoromethylthio, trichloromethylthio, 2-chloro-1,1,2-trifluoroethylthio or pentafluoroethylthio;

(d) phenyl which may carry from one to four of the following groups: $C_1$–$C_4$-alkyl as stated above, in particular methyl, ethyl or 1-methylethyl; partially or completely halogenated $C_1$–$C_4$-alkyl as stated above, in particular trifluoromethyl or chlorodifluoromethyl; $C_1$–$C_4$-alkoxy as stated above, in particular methoxy or ethoxy; partially or completely halogenated $C_1$–$C_4$-alkoxy as stated above, in particular trifluoromethoxy, trichloromethoxy or pentafluoroethoxy; $C_1$–$C_4$-alkylthio as stated above, in particular difluoromethylthio, trifluoromethylthio or pentafluoromethylthio, halogen, as stated above, in particular fluorine and chlorine, cyano, nitro, formyl, $C_1$–$C_4$-alkanoyl, such as acetyl, propionyl or butyryl, in particular acetyl, partially or completely halogenated alkanoyl, such as trifluoroacetyl, trichloroacetyl or pentafluoropropionyl, in particular trifluoroacetyl, or alkoxycarbonyl, such as methoxycarbonyl or tert-butoxycarbonyl;

and the plant-tolerated salts of those compounds in which $R^2$ is hydrogen.

Suitable salts of the compounds of the formula I are agriculturally useful salts, for example alkali metal salts, in particular sodium and potassium salts, alkaline earth metal salts, such as in particular calcium, magnesium and barium salts, manganese, copper, zinc or iron salts and ammonium salts, such as tetraalkyl- and benzyltrialkylammonium salts, phosphonium salts, phosphonium salts, sulfonium salts, such as trialkylsulfonium salts, or sulfoxonium salts.

The compounds I or the herbicides containing them and their environmentally compatible salts of alkali metals and alkaline earth metals can control weeds and grass weeds very well in crops such as wheat, rice, corn, soybean and cotton, without damaging the crops, an effect which occurs in particular at low application rates.

The compounds I or the herbicides containing them can be applied, for example, in the form of directly sprayable aqueous solutions, powders, suspensions, including concentrated aqueous, oily or other suspensions or dispersions, emulsions, oil dispersions, pastes, dusts, broadcasting agents or granules, by spraying, nebulizing, dusting, broadcasting or pouring. The application forms depend on the intended uses; they should in any case ensure a very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, as well as coal tar oils and oils of vegetable or animal origin, aliphatic, cyclic and aromatic hydrocarbons, for example paraffin, terahydronaphthalene, alkylated naphthalenes or derivatives thereof, methanol, ethanol, propanol, butanol, cyclohexanol, cyclohexanone or strongly polar solvents, N-methylpyrrolidone or water.

Aqueous application forms can be prepared from emulsion concentrates, suspensions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsiifiers. However, concentrates consisting of active ingredient, wetting agents, adherents, dispersants or emulsifiers and possibly solvents or oil and suitable for dilution with water can also be prepared.

Suitable surfactants are the alkali metal, alkaline earth metal or ammonium salts of aromatic sulfonic acids, for example lignin-, phenol-, naphthalene- and dibutylnaphtahlenesulfonic acid, and of fatty acids, alkyl- and alkylarylsulfonates, alkylsulfates, lauryl ether sulfates and fatty alcohol sulfates, and salts of sulfated hexa-, hepta- and octadecanols and of fatty alcohol glycol ethers, condensates of sulfonated naphthalene and its derivatives with formaldehyde, condensates of naphthalene or of naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents and dusts can be prepared by mixing or milling the active ingredients together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders and other solid carriers.

The formulations contain in general from 0.01 to 95, preferably from 0.5 to 90, % by weight of active ingredient. The active ingredients are used in a purity of from 90 to 100%, preferably from 95 to 100% (according to the NMR spectrum).

The novel compounds I may be formulated, for example, as follows:

I. 20 parts by weight of compound No. 1.001 are dissolved in a mixture which consists of 80 parts by weight of alkylated benzene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

II 20 parts by weight of compound No. 1.001 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III 20 parts by weight of active ingredient No. 1.001 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV 20 parts by weight of active ingredient No. 1.001 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

V 3 parts by weight of active ingredient No. 1.001 are mixed with 97 parts by weight of finely divided kaolin. A dust which contains 3% by weight of the active ingredient is obtained in this manner.

VI 20 parts by weight of active ingredient No. 1.001 are intimately mixed with 97 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients may be applied by the preemergence or the postemergence method. If the active ingredients are less well tolerated by certain crops, it is possible to use application methods in which the herbicides are sprayed with the aid of the sprayers in such a way that there is very little contact with the leaves of the sensitive crops whereas the active ingredients reach the leaves of undesirable plants growing underneath or the uncovered soil surface (post-directed, lay-by).

The application rates of active ingredient are from 0.001 to 5.0, preferably from 0.01 to 2.0, kg/ha of active ingredient (a.i.), depending on the aim of control, the season, the target plants and the stage of growth.

In view of the versatility of the application methods, the compounds I or agents containing them can also be used in a further number of crops for eliminating undesirable plants. For example, the following crops are suitable:

| Botanical name | Common name |
| --- | --- |
| Allium cipa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |
| Camellia sinensis | tea plants |
| Carthamus tinctorius | safflower |
| Carya illinoinensis | pecan trees |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| picea abies | Norway spruce |

| Botanical name | Common name |
| --- | --- |
| Pinus spp. | pine trees |
| Pisum sativum | garden peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To broaden the action spectrum and to achieve synergistic effects, the isoxazolecarboxamides of the general formula I can be mixed with a large number of other herbicidal or growth-regulating active ingredients and applied together with them. Examples of suitable components for the mixture are diazines, 4H-3,1-benzoxazine derivatives, benzothiadiazinones, 2,6-dinitroanilines, N-phenylcarbamates, thiocarbamates, halo-carboxylic acids, triazines, amides, ureas, diphenyl ethers, triazinones, uracils, benzofuran derivatives, cyclohexane-1,3-dione derivatives, which carry, for example, a carboxyl or carbimino group in the 2-position, quinolinecarboxylic acid derivatives, imidazolinones, sulfonamides, sulfonylureas, aryloxy- and hetaryloxy-phenoxypropionic cids and their salts, esters and amides and others.

It may also be useful to apply the compounds I, alone or in combination with other herbicides, also as a mixture with further crop protection agents, for example with pesticides or agents for controlling phytopathogenic fungi or bacteria. The miscibility with mineral salt solutions which are used for eliminating nutrient and trace element deficiencies is also of interest. Non-phytotoxic oils and oil concentrates may also be added.

SYNTHESIS EXAMPLES

Preparation of hydroxamoyl chlorides III:
Cyclopropylcarbamoylformhydroxamoyl chloride

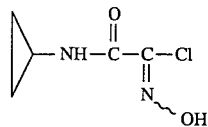

28.5 g (0.5 mol) of cyclopropylamine in 500 ml of water are initially taken at room temperature and 42.0 g (0.5 mol) of diketene are then added dropwise. The pH decreases from 12.0 to 5.5–6.6. Stirring is carried out for 10 minutes, 37.9 g (0.55 mol) of sodium nitrite are added and about 75 ml of concentrated hydrochloric acid are then introduced so that the pH always remains above 4.5. After the addition is complete, 41.1 g (0.58 mol) of elemental chlorine are passed in as a gas at room temperature. Monitoring for complete conversion is carried out by TLC or HPLC. The hydroxamoyl chloride formed in the reaction can be isolated either by filtration at 0° C. or by repeated extraction with ethyl acetate and removal of the solvent under reduced pressure. The solid thus obtained is washed with water and dried at not more than 40° C. under reduced pressure. 72.1 g (89%) of cyclopropylcarbamoylformhydroxamoyl chloride are obtained as a white solid.

$^1$H-NMR (250 MHz, DMSO): δ=0.50–0.78 (m; 4H), 2.75 (m; 1H), 8.48 (d; 1H, NM), 12.80 (s; 1H, OH)

Preparation of the isoxazolecarboxamides I:
Methyl 3-tert-butylaminocarbonylisoxazole-4-carboxylate (Example 1.001)

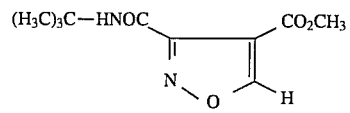

15.5 g (0.1 mol) of methyl 3-(1-pyrrolidinyl)acrylate are dissolved in 200 ml of tetrahydrofuran, and 17.8 g (0.1 mol) of tert-butylcarbamoylformhydroxamoyl chloride in 200 ml of tetrahydrofuran are added. Refluxing is carried out for about 3 hours. Thereafter, the mixture is diluted with water, rendered alkaline with sodium hydroxide solution, stirred for 5 minutes and then acidified again with hydrochloric acid. The solution is extracted with ethyl acetate and the organic phase is washed with 2N hydrochloric acid and with water. Purification is carried out by chromatography over silica gel. Yield 12.9 g. Mp. 91°–93° C.

Methyl 3-tert-butylaminocarbonylisoxazole-4-carboxylate (Example 1.001)

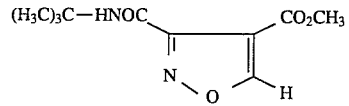

64.5 g (0.5 mol) of methyl 3-dimethylaminoacrylate are dissolved in 200 ml of tetrahydrofuran, and 90.0 g (0.5 mol) of tert-butylcarbamoylformhydroxamoyl chloride in 200 ml of tetrahydrofuran are added. Refluxing is carried out for about 3 hours. Thereafter, the mixture is diluted with water, rendered neutral with sodium hydroxide solution, stirred for 5 minutes and then acidified again with hydrochloric acid. The solution is extracted with ethyl acetate and the organic phase is washed with 2N hydrochloric acid and with water, dried and evaporated down. Yield 110 g. Mp. 91°–93° C.

3-tert-Butylaminocarbonylisoxazole-4-carboxylic acid

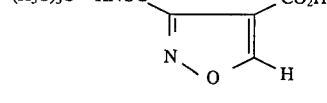

7.2 g (0.032 mol) of methyl 3-tert-butylaminocarbonyl-isoxazole-4-carboxylate are dissolved in 80 ml of methanol, and 1.34 g (0.033 mol) of sodium hydroxide in 50 ml of water are added at 0° C. The mixture is stirred for 12 hours and then diluted with water, brought to pH 1 with hydrochloric acid and extracted three times with ethyl acetate. The organic phase is dried over magnesium sulfate and evaporated down. The yield comprises 5.7 g of an oil, which can be used without further purification in the subsequent reactions.

Propargyl 3-tert-butylaminocarbonylisoxazole-4-carboxylate (Example 1.010)

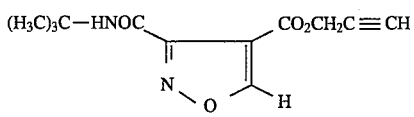

4.3 g (0.02 ml) of 3-tert-butylaminocarbonylisoxazole-4-carboxylic acid and 1.5 g (0.0265 mol) of propargyl alcohol are dissolved in 150 ml of ethyl acetate, and 7.6 g (0.075 mol) of N-methylmorpholine and 2.5 g (0.02 mol) of N,N-dimethylaminopyridine are added. The mixture is stirred for five minutes at room temperature, after which 17.8 g of a 50% strength propanephosphonic anhydride solution in dichloromethane are added dropwise and stirring is then continued for eight hours at 45° C. and for a further 14 hours at room temperature. For working up, the solution is extracted with saturated aqueous sodium bicarbonate solution and citric acid solution, dried over magnesium sulfate and evaporated down and the residue is chromatographed over silica gel. Yield 3 g.

3-tert-Butyl 4-ethyl isoxazole-3,4-dicarboxylate

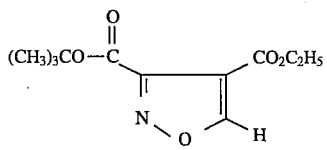

87.7 g (0.52 mol) of ethyl 3-(1pyrrolidinyl) acrylate are dissolved in 500 ml of tetrahydrofuran, and 93.2 g (0.52 mol) of tert-butyl 2-chloro-2-hydroximino-acetate in 500 ml of tetrahydrofuran are added. Refluxing is carried out for about 3 hours. Thereafter, the mixture is diluted with water, rendered neutral with sodium hydroxide solution, stirred for 5 minutes and then acidified again with hydrochloric acid. The solution is extracted with ethyl acetate and the organic phase is washed with 2N hydrochloric acid and with water. Purification is carried out by chromatography over silica gel. 50.6 g of an oil are obtained.

4-Ethyl isoxazole-3,4-dicarboxylate

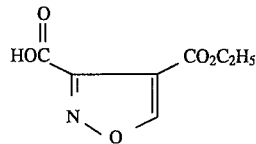

30 g (0.125 mol) of 3-tert-butyl 4-ethylisoxazole-3,4-dicarboxylate in 600 ml of dichloromethane and 60 ml of trifluoroacetic acid are stirred for two hours at room temperature. The reaction solution is poured in 1 l of water, and the organic phase is separated off, extracted several times with water, dried and evaporated down. 21 g of an oil which is used without further purification are obtained.

Ethyl 3-chlorocarbonylisoxazole-4-carboxylate

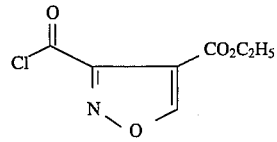

16.9 g (0.09 mol) of 4-ethyl isoxazole-3,4-dicarboxylate are dissolved in 200 ml of toluene, 21.7 g (0.18 mol) of thionyl chloride are added and refluxing is carried out for 2 hours. Thereafter, the mixture is evaporated to dryness and the oil obtained (17.4 g) is reacted without further purification.

Ethyl 3-(1,1-dimethylpropargylaminocarbonyl)-isoxazole-4-carboxylate (Example 1.027)

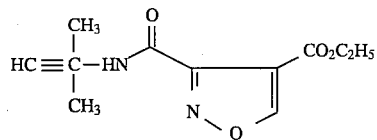

5.8 g (0.028 mol) of ethyl 3-chlorocarbonylisoxazole-4-carboxylate are dissolved in 100 ml of toluene, the solution is cooled to 0°–10° C. and 4.73 g (0.057 mol) of 1,1-dimethylpropargylamine are added. Stirring is carried out for a few hours at room temperature, after which water is added to the solution and the organic phase is separated off and extracted with aqueous citric acid and aqueous sodium bicarbonate solution. The organic phase is then evaporated to dryness and the residue obtained is purified by chromatography over silical gel. Yield 3.5 g, mp. 75°–82° C.

The compounds shown in Table I were prepared similarly to the above examples.

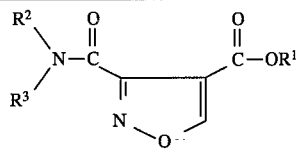

| Ex. No. | $R^1$ | $R^2$ | $R^3$ | m.p. [°C.] $^1$H-NMR/CDCl$_3$ or DMSO δ [ppm] |
|---------|-------|-------|-------|------|
| 1.001 | CH$_3$ | H | C(CH$_3$)$_3$ | 91–93 |
| 1.002 | CH$_3$ | H | Cyclopropyl | 3,05(m, 1H); 3,94(s, 3H); |
| 1.003 | CH$_3$ | CH$_3$ | CH$_3$ | 82–84 |
| 1.004 | CH$_3$ | CH$_3$ | C$_2$H$_5$ | 1,20 u. 1,30(2t, 3H); 2,90 u. 3,15(2s, 3H); |
| 1.005 | C$_2$H$_5$ | H | C(CH$_3$)$_3$ | 85–88 |

-continued

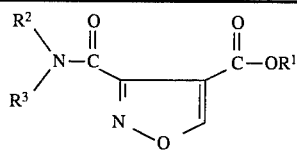

I

| Ex. No. | R¹ | R² | R³ | m.p. [°C.]<br>¹H-NMR/CDCl₃ or<br>DMSO δ [ppm] |
|---|---|---|---|---|
| 1.006 | CH₂CH₂OCH₃ | H | C(CH₃)₃ | 3,35(s, 3H); 3,70(t, 2H); 4,45(t, 2H); |
| 1.007 | CH₃ | H | CH(CH₃)₂ | 92–96 |
| 1.008 | CH₃ | H | CH(CH₃)C₂H₅ | 93–96 |
| 1.009 | CH₂CH=CH₂ | H | C(CH₃)₃ | 58–60 |
| 1.010 | CH₂—C≡CH | H | C(CH₃)₃ | 2,55(m, 1H); 9,05(s, 1H) |
| 1.011 | C₂H₅ | H | CH(CH₃)C₂H₅ | 81–83 |
| 1.012 | CH₂—C₆H₅ | H | C(CH₃)₃ | 1,45(s, 9H); 5,35(s, 2H) |
| 1.013 | CH₂—(4-Cl—C₆H₄) | H | C(CH₃)₃ | 95–103 |
| 1.014 | CH₂CH₂CH₃ | H | C(CH₃)₃ | 58–60 |
| 1.015 | CH(CH₃)₂ | H | C(CH₃)₃ | 99–101 |
| 1.016 | C₂H₅ | H | Cyclopropyl | 65–70 |
| 1.017 | CH(CH₃)₂ | H | Cyclopropyl | 114–115 |
| 1.018 | CH₂—C₆H₅ | H | Cyclopropyl | 98–100 |
| 1.019 | cyclopentylidene-N= | H | Cyclopropyl | 119–121 |
| 1.020 | CH₂—C≡CH | H | CH(CH₃)C₂H₅ | 2.60(t, 1H); 9,10(s, 1H) |
| 1.021 | CH₂CH₂OCH₃ | H | CH(CH₃)C₂H₅ | 1,00(t, 3H); 3,22(s, 3H) |
| 1.022 | CH₂—CH=CH₂ | H | CH(CH₃)C₂H₅ | 49–52 |
| 1.023 | CH(CH₃)C₃H₅ | H | CH₃ | 83–87 |
| 1.024 | CH₂CH=CH₂ | H | CH(CH₃)C₃H₅ | 1,05(d, 3H); 5,60–5,80 (m, 1H) |
| 1.025 | C₂H₅ | H | CH(CH₃)C₃H₅ | 97–98 |
| 1.026 | CH₂—C≡CH | H | CH(CH₃)C₃H₅ | 1.35(d, 3H); 2,60(t, 1H) |
| 1.027 | C₂H₅ | H | C(CH₃)₂C≡CH | 75–82 |
| 1.028 | C₂H₅ | H | C(CH₃)₂CN | 76–78 |
| 1.029 | C₂H₅ | H | 3-CF₃—C₆H₄ | 96–97 |
| 1.030 | CH₂CH₂Cl | H | CH(CH₃)C₃H₅ | 79–82 |
| 1,031 | CH₂C₆H₅ | H | CH(CH₃)C₃H₅ | 1,30(d, 3H); 5,35(s, 2H) |
| 1.032 | (CH₂)₄CH₃ | H | C(CH₃)₃ | 1,40(s, 9H); 4.35(t, 2H) |
| 1.033 | C₆H₁₁ | H | C(CH₃)₃ | 1,50(s, 9H); 5,00(m, 1H) |
| 1.034 | C₂H₅ | H | C₆H₅ | 108–115 |
| 1.035 | C₂H₅ | H | 4-Cl—C₆H₄ | 100–105 |
| 1.036 | CH₂C≡CCH₃ | H | C(CH₃)₃ | 85–90 |
| 1.037 | CH₂-(4-CH₃—C₆H₄) | H | C(CH₃)₃ | 3,80(s, 3H); 8,95(s, 1H) |
| 1.038 | CH(CH₃)CH=CH₂ | H | C(CH₃)₃ | 1,50(s, 9H); 5,55(m, 1H) |
| 1.039 | CH₂CCl₃ | H | C(CH₃)₃ | 4,95(s, 2H); 9,15(s, 1H) |
| 1.040 | CH₂CH₂OCH₂CH₂Cl | H | C(CH₃)₃ | 4,45(m, 2H); 9,05(s, |

-continued

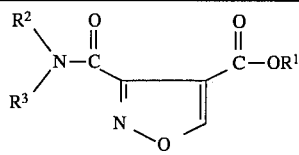

| Ex. No. | R¹ | R² | R³ | m.p. [°C.] ¹H-NMR/CDCl₃ or DMSO δ [ppm] |
|---|---|---|---|---|
| 1.041 | CH₂CH=C(CH₃)₂ | H | C(CH₃)₃ | 4,80(d, 2H); 9,00(s, 1H) |
| 1.042 | (CH₂)₂C≡CH | H | C(CH₃)₃ | 2,35(m, 2H); 4,45(t, 2H) |
| 1.043 | (CH₂)₂C≡CH | H | C(CH₃)₃ | 2,70(m, 2H); 9,00(s, 1H) |
| 1.044 | CH₂C(CH₃)=CH₂ | H | C(CH₃)₃ | 1,85(s, 3H); 4,75(s, 2H) |
| 1.045 | CH₂C(CH₃)₃ | H | C(CH₃)₃ | 87 |
| 1.046 | CH₂C(Cl)CH₃ | H | C(CH₃)₃ | 1,50(s, 9H); 5,30(m, 1H |
| 1.047 | CH₂C≡CCH₂Cl | H | C(CH₃)₃ | 1,50(s, 9H); 5,00(m, 2H) |
| 1.048 | (CH₂)₃CH₂Cl | H | C(CH₃)₃ | 1,50(s, 9H); 3.60 m, 2H) |
| 1.049 | CH₂—⟨tetrahydrofuran-2-yl⟩ | H | C(CH₃)₃ | 1,50(s, 9H); 3.80–3,95(m, 2H) |
| 1.050 | CH₂CF₃ | H | C(CH₃)₃ | 4,70(q, 2H); 9,05(s, 1H) |
| 1.051 | CH₂C(C₂H₅)=CH₂ | H | C(CH₃)₃ | 1,10(t, 3H); 2,15(q, 2H) |
| 1.052 | CH₂—⟨3-isopropyl-isoxazolin-5-yl⟩ | H | C(CH₃)₃, | 1,20(d, 6H); 4,90(m, 1H) |
| 1.053 | CH₂CH₂SCH₃ | H | C(CH₃)₃ | 2,15(s, 3H); 4,45(t, 3H) |
| 1.054 | C₂H₅ | H | CH₂C=CH₂ \| CH₃ | 4,05(d, 2H); 9,05(s, 1H) |
| 1.055 | C₂H₅ | H | C(CH₃)CH=CH₂ \| CH₃ | 1,60(s, 6H); 4,40(q, 2H) |
| 1.056 | C₂H₅ | H | C₂H₅ \| C—C≡CH \| C₂H₅ | 1,05(t, 6H); 1,40(t, 3H) |
| 1.057 | C₂H₅ | H | C(CH₃)C≡CH \| C₃H₇ | 1,75(s, 3H); 2,45(s, 1H) |
| 1.058 | C₂H₅ | H | CH₃  CH₃ \|    \| C——CH \|    \| CH₃  CH₃ | 63–68 |
| 1.059 | ⟨2-chlorocyclohexyl⟩ | H | C(CH₃)₃ | 1,50(s, 9H); 4,95(m, 1H) |
| 1.060 | C₂H₅ | | H | 1-Methylcy- | 114–118 |

-continued

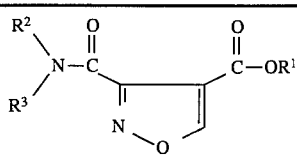

| Ex. No. | R¹ | R² | R³ | m.p. [°C.] ¹H-NMR/CDCl₃ or DMSO δ [ppm] |
|---|---|---|---|---|
| | | | clopropyl | |
| 1.061 | CH₂CH=CHCC≡CH<br>          \|<br>          CH₃ | H | C(CH₃)₃ | 1,95(s, 3H);<br>4,85(d, 2H) |
| 1.062 | C₂H₅ | H | CH(CH₃)₂ | 81–87 |
| 1.063[2)] | C₂H₅ | H | CH(CH₃)C₃H₅ | 95–100 |
| 1.064 | C₂H₅ | H | CH(CH₂)₂C₆H₅<br>\|<br>CH₃ | 1,35(d, 3H);<br>4,40(q, 2H) |
| 1.065 | C₂H₅ | H | CH₂CHCH₃<br>\|<br>(CH₂)₂C₆H₅ | 0,95(d, 3H);<br>9,00(s, 1H) |
| 1.066[1)] | C₂H₅ | H | CH(CH₃)C₃H₅ | 98–105 |
| 1.067 | CH₂C≡CH | H | CH(CH₂)₂C₆H₅<br>\|<br>CH₃ | 1,30(d, 3H);<br>4,90(d, 2H) |
| 1.068 | C₂H₅ | H | CH(CH₃)C₆H₅ | 1,20(t, 3H);<br>9,40(d, 2H) |
| 1.069[1)] | C₂H₅ | H | CH(CH₃)C₆H₅ | 1,20(t, 3H);<br>9,40(d, 2H) |
| 1.070[2)] | C₂H₅ | H | CH(CH₃)C₆H₅ | 1,20(t, 3H);<br>9,40(d, 2H) |
| 1.071 | N= (cyclohexylidene) | H | C(CH₃)₃ | 1,35(s, 9H);<br>1,75(m, 4H) |
| 1.072 | N= (cyclopentylidene) | H | C(CH₃)₃ | 1,35(s, 9H);<br>9,80(s, 1H) |
| 1.073 | CH₂CH₂ON=C(CH₃)₂ | H | C(CH₃)₃ | 1,40(s, 9H);<br>4,15(m, 2H) |
| 1.074 | CH₂CH₂C=CH₂<br>         \|<br>         CH₃ | H | C(CH₃)₃ | 1,75(s, 3H);<br>4,35(t, 3H) |
| 1.075 | CHCH₂ON=C(CH₃)₂<br>\|<br>CH₃ | H | C(CH₃)₃ | 85–86 |
| 1.076 | phthalimido (N-bonded) | H | C(CH₃)₃ | |
| 1.077 | —N=C(CH₃)₂ | H | C(CH₃)₃ | |
| 1.078 | CH₂CH₂Si(CH₃)₃ | H | C(CH₃)₃ | |
| 1.079 | CH₂CH₂N(CH₃)₂ | H | C(CH₃)₃ | |
| 1.080 | CH₂CH=NOC₂H₅ | H | C(CH₃)₃ | |
| 1.081 | CHCO₂CH(CH₃)₂<br>\|<br>CH₃ | H | C(CH₃)₃ | |
| 1.082 | CH(CH₃)CO₂CH₃ | H | C(CH₃)₃ | |
| 1.083 | CH(CH₃)CONH₂ | H | C(CH₃)₃ | |
| 1.084 | C₆H₅ | H | C(CH₃)₃ | 77–79 |

-continued

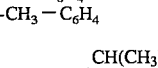

| Ex. No. | R¹ | R² | R³ | m.p. [°C.]<br>¹H-NMR/CDCl₃ or<br>DMSO δ [ppm] |
|---|---|---|---|---|
| 1.085 | 4-Cl—C₆H₄ | H | C(CH₃)₃ | 135 |
| 1.086 | 4-CH₃—C₆H₄ | H | C(CH₃)₃ | 102–103 |
| 1.087 | 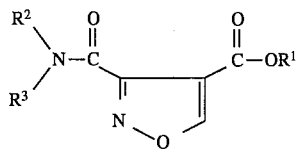 | H | C(CH₃)₃ | |

[1)](+)-Enantiomer,
[2)](−)-Enantiomer

Use Examples

It was possible to demonstrate the herbicidal action of the isoxazolecarboxamides of the general formula I by greenhouse experiments: The culture vessels used were plastic flowerpots containing loamy sand with about 3.0% of humus as the substrate. The seeds of the test plants were sown separately according to species.

For the purpose of the postemergence treatment, the test plants are first grown to a height of growth of from 3 to 15 cm, depending on the form of growth, before being treated with the active ingredients suspended or emulsified in water. For this purpose, the test plants are either directly sown and grown in the same vessels or are first grown separately as seedlings and transplanted into the test vessels a few days before the treatment. The application rate for the postemergence treatment is 3.0 kg/ha of a.i.

The plants were kept at from 10° to 25° C. or from 20° to 35° C., according to species. The test period extended over 2–4 weeks. During this time, the plants were tended and their reaction to the individual treatments was evaluated.

Rating was based on a scale from 0 to 100. 100 means no emergence of the plants or complete destruction of at least the above-ground parts, and 0 means no damage or normal growth.

The plants used in the greenhouse experiments consisted of the following species:

| Botanical name | Common name | Abbreviation |
|---|---|---|
| *Centaurea cyanus* | cornflower | CENCY |
| *Galium aparine* | catchweed bedstraw | GALAP |
| *Viola* ssp. | pansy | VIOSS |

The following comparison in Table 1 demonstrates the superior herbicidal action of the novel compound No. 1.001 in comparison with the comparative compound A disclosed in EP-A 418 667, Example No. 3.116.

TABLE 1

Example for the control of undesirable broad-leaved plants by postemergence application of 3.0 kg of a.i./ha in the greenhouse

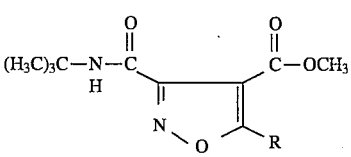

| Example No. | 1.001 | A |
|---|---|---|
| R | H | CH₃ |
| Application rate (kg/ha a.i.) | 3.0 | 3.0 |
| Test plants (damage in %) | | |
| CENCY | 100 | 0 |
| GALAP | 95 | 0 |
| VIOSS | 100 | 0 |

We claim:

1. An isoxazolecarboxamide of the formula I

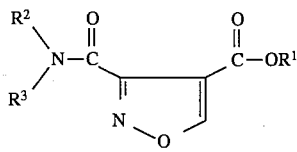

where
R¹ is unsubstituted C₁–C₆-alkyl;
R² is hydrogen;
R³ is unsubstituted C₁–C₆-alkyl;
or the plant-tolerated salts thereof.

2. An isoxazolecarboxamide of the formula I as defined in claim 1, wherein R³ is —C(CH₃)₃.

3. A composition containing a herbicidally effective amount of an isoxazolecarboxamide of the formula I as defined in claim 1 and inert additives.

4. A method for controlling undesirable plant growth, wherein the plants or their habitat is or are treated with a herbicidal amount of an isoxazolecarboxamide of the formula I as defined in claim 1.

5. A method for controlling undesirable plant growth wherein the plants or their habitat is or are treated with a herbicidal amount of an isoxazolecarboxamide of the formula I as defined in claim 2.

\* \* \* \* \*